(12) United States Patent
Domenico et al.

(10) Patent No.: US 6,380,248 B1
(45) Date of Patent: Apr. 30, 2002

(54) METAL-THIOLS AS IMMUNOMODULATING AGENTS

(75) Inventors: Philip Domenico, Elmhurst; Dhanonjoy Saha, Brooklyn, both of NY (US)

(73) Assignee: Winthrop University Hospital, NY (US)

( * ) Notice: Subject to any disclaimer, the term of this patent is extended or adjusted under 35 U.S.C. 154(b) by 0 days.

(21) Appl. No.: 09/601,491

(22) PCT Filed: Feb. 3, 1999

(86) PCT No.: PCT/US99/02374

§ 371 Date: Dec. 14, 2000

§ 102(e) Date: Dec. 14, 2000

(87) PCT Pub. No.: WO99/39707

PCT Pub. Date: Aug. 12, 1999

Related U.S. Application Data

(60) Provisional application No. 60/073,677, filed on Feb. 4, 1998.

(51) Int. Cl.⁷ .................. A61K 31/29; A61K 31/285
(52) U.S. Cl. ......................... 514/503; 514/504
(58) Field of Search ............................ 514/503, 504

(56) References Cited

U.S. PATENT DOCUMENTS

| | | | |
|---|---|---|---|
| 4,923,643 A | 5/1990 | Efner | 260/410 |
| 5,690,905 A | 11/1997 | Zamora et al. | 424/1.69 |

*Primary Examiner*—Raymond Henley, III
(74) *Attorney, Agent, or Firm*—Ostrolenk, Faber, Gerb & Soffen, LLP

(57) ABSTRACT

A method is described to treat or prevent sepsis and septic shock in a subject by administering a Group V metal chelated by a complexing agent such as thiol compounds in the form of a metal:complexing agent, wherein the metal is selected from the group consisting of bismuth, antimony and arsenic. Methods for modulating the immune system are also disclosed.

19 Claims, 5 Drawing Sheets

METAL-THIOLS AS IMMUNOMODULATING AGENTS

This application is a 371 of PCT/US99/02374 filed Feb. 3, 1999 which is based upon and claims priority of U.S. Provisional Application No. 60/073,677, filed Feb. 4, 1998, which are each hereby incorporated by reference.

FIELD OF THE INVENTION

The present invention relates to a method for the treatment and prevention of sepsis and septic shock by using metal:thiol complexes. The present invention also relates to the use of metal:thiol complexes to modulate the immune system.

DESCRIPTION OF THE RELATED ART

Sepsis results from an infection and is manifested clinically by fever or hypothermia, increased heart and respiratory rates, abnormal white blood cell count, and evidence of systemic hypoperfusion. It is accompanied by a number of cellular and biochemical changes in the immune system. Septic shock is a condition that usually develops as a complication of overwhelming sepsis. Worldwide statistics on sepsis or septic shock are not known. However, sepsis is a frequent cause of death in the USA and accounts for a substantial health-related costs annually. A study of sepsis and septic shock between 1979–1987 has demonstrated a progressive increase in their incidence despite the development of more potent antibiotics, supportive therapy and critical care medicine. Although precise recent data are not available, it was estimated that 100,000 to 400,000 patients develop sepsis annually in the United States; half of these patients develop septic shock with a mortality rate ranging between 20% and 80% depending upon the definition of the syndrome. More than 70–80% of all cases of septic shock were caused by gram-negative organisms. However, recent trends show an increase in the incidence of gram positive bacteria (30–40%), virus- and fungi-related sepsis which previously were considered to be minority causes of sepsis.

Many therapies that have been used to treat or prevent septic shock have proven insufficient. These approaches include (1) eliminating the causal agents (that cause the release of toxins and cell wall product), or (2) using antibodies against the inflammatory mediators. It has been theorized that morbidity and mortality from sepsis and septic shock arise from emergence of the anti-inflammatory cytokines or mediators that cause immunosuppression. It has been suggested that boosting the immune system may prove beneficial. However, any attempt to put this into clinical practice risks inflammatory effects of the agents used, in a compromised system.

Bismuth has been known for many years as an antibacterial agent and has been used against *Helicobacter pylori*. The subcitrate forms of Bismuth are used as anti-diarrheal and anti-septic agents and some other purposes. The potency or efficacy of these compounds are low, especially in the presence of iron. In addition, insolubility of Bismuth in water decreased its effectiveness substantially thus restricting its use.

SUMMARY OF THE INVENTION

It is an object of the present invention to provide methods to treat and prevent sepsis and septic shock.

It is another object of the invention to provide methods to modulate the immune system.

In one embodiment, the invention provides a method of treating or preventing sepsis or septic shock by administering to a subject in need of such treatment or prevention, a formulation comprising an immunomodulating agent selected from the group consisting of:

(A) a mixture comprising (i) a complexing agent having at least one thiol group, and (ii) a group V metal or compound thereof said Group V metal being selected from the group consisting of bismuth, antimony and arsenic;

(B) a complex whose molecular structure includes (i) a complexing agent having at least one thiol group, (ii) a Group V metal or compound thereof said Group V metal being selected from the group consisting of bismuth, arsenic and antimony; and (iii) a coordinate bond linking at least one sulfur atom of the thiol-containing complexing agent of subparagraph (B)(i) to the metal of subparagraph (B)(ii); and (C) a combination comprising the complex of paragraph (B) and at least one specie selected from the group consisting of (i) a thiol-containing complexing agent and (ii) a Group V metal or compound thereof, said Group V metal, being selected from the group consisting of bismuth antimony and arsenic.

The term "thiol" is used herein to refer to a compound that contains one or more sulfur atoms capable of existing in the form of sulfhydryl groups under appropriate pH conditions, regardless of whether such sulfur atoms are deprotonated or fully or partially protonated under conditions in which the thiol is used, and regardless of the pH under which it is used. "Thiol group" means a sulfur or an —SH group of a "thiol".

The terms "mixture" and "combination" encompass the use of two or more components in sufficiently close proximity to each other that they may interact with each other under conditions of end use for the immunomodulating agent of the invention, or for products which include said agent in accordance with the invention. Patients in need of treatment for a particular disease are those displaying symptoms or responding to diagnostic tests indicating presence of the disease in question. Patients in need of prophylactic intervention are those who through exposure or otherwise are at higher risk of contracting the disease in question than is the general population.

Immunomodulating agents described herein may be used to modulate the immune system and more specifically to prevent or alleviate an immunosuppression state which can occur for example in sepsis and septic shock.

In another embodiment, the invention provides a method of modulating the immune response in a subject comprising administering to said subject a formulation comprising an immunomodulating agent selected from the group consisting of:

(A) a mixture comprising (i) a complexing agent having at least one thiol group, and (ii) a group V metal or compound thereof said Group V metal being selected from the group consisting of bismuth, antimony and arsenic;

(B) a complex whose molecular structure includes (i) a complexing agent having at least one thiol group, (ii) a Group V metal or compound thereof said Group V metal being selected from the group consisting of bismuth, arsenic and antimony; and (iii) a coordinate bond linking at least one sulfur atom of the thiol-containing complexing agent of subparagraph (B)(i) to the metal of subparagraph (B) (ii); and (C) a combination comprising the complex of paragraph (B) and at least one specie selected from the group consisting of (i) a thiol-containing complexing agent and (ii) a Group V metal or compound thereof, said Group V metal, being selected from the group consisting of bismuth, antimony and arsenic.

Other features and advantages of the present invention will become apparent from the following description of the invention which refers to the accompanying drawings.

DETAILED DESCRIPTION OF THE INVENTION

Figure 1:
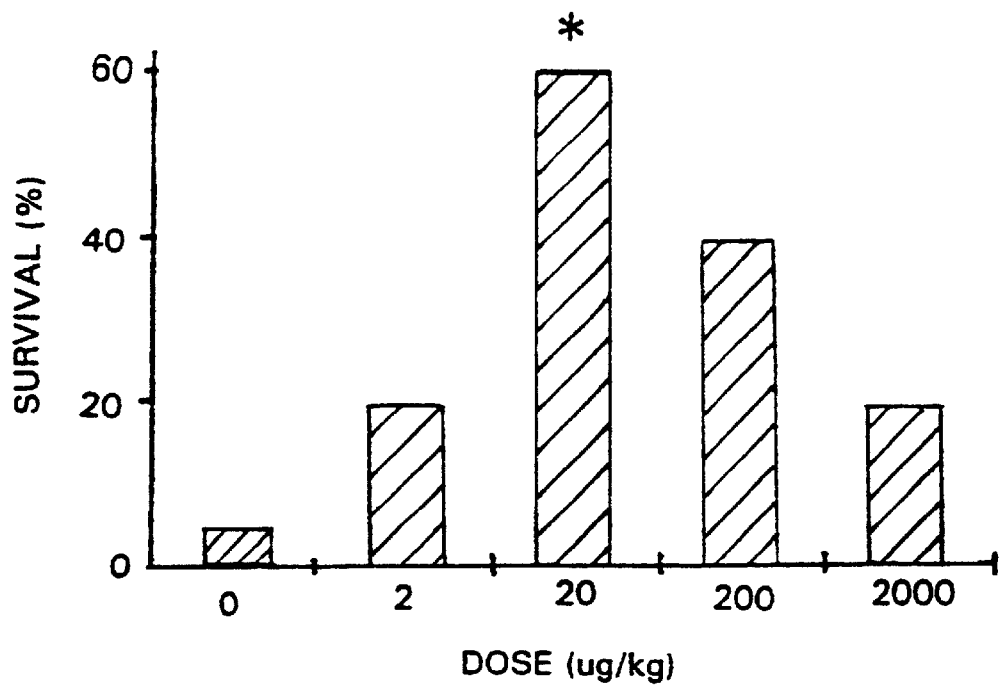
FIG. 1 shows the survival rate of mice weighing approximately 30 g where sepsis was induced by cecal ligation and perforation (CLP mice) and then treated with different doses of BisEDT. In the absence of any treatment, mortality rate is greater than 90% within 18–72 hours.

In accordance with the invention, a Group V metal and a thiol provide a surprising immunomodulation activity. Applicants found that a Group V metal:thiol combination increases metal solubility, lowers metal toxicity and increases anti-bacterial effects. In addition, applicants also found that a Group V metal:thiol combination binds lipopolysaccharide, the primary mediator of sepsis/septic shock. Furthermore, in low doses (2–3 parts per million), this combination showed bacteriostatic effects with no lytic action. Bismuth-thiol combinations were found by applicants to have selective effects on the expression of virulence factors in bacteria. Furthermore, low doses (1–3 parts per million) inhibited bacterial growth and decreased capsular polysaccharide development in *Klebsiella pneumoniae* and other members of the Enterobacteriaceae family.

Internal use of a combination of a Group V metal and a thiol provides a method of suppressing or killing microbial agents while not liberating toxins or harmful cellular fragments. Without intending to be bound by theory, it appears to maintain cellular integrity of the host cell (i.e. the cells of the subject being treated) and microbial cell, and maintains a balance between the pro-inflammatory and anti-inflammatory cytokines and mediators, thus preventing immune suppression.

The antimicrobial or immunomodulatory property of the agent may be used to suppress microbial growth, reduce microbial load or eliminate microorganisms without releasing toxins or cellular degradation products. Host cell integrity is maintained when the agent is used.

Without intending to be bound by theory, it is believed that the immunomodulating activity of a Group V metal and a thiol is the result of: 1) the ability to maintain host and microbial cell integrity, while binding released toxins: and/or 2) preventing or reducing the up-regulation of both pro- and anti-inflammatory cytokines that occur in polymicrobial sepsis. The antimicrobial activity of a Group V metal and a thiol is manifested in the ability to reduce microbial load, eliminate microorganisms without releasing toxins or cellular degradation products into the host's body, an event that can cause sepsis and septic shock. Thus a Group V metal and a thiol play a role in preventing sepsis and septic shock.

Again without intending to be bound by theory, it is also believed that in certain embodiments of the invention, the metal and thiol form a complex having a coordinate bond between the metal and at least one sulfur atom of the thiol. Formation of this complex may provide several different advantages. For example, the complex may have a more suitable solubility in both hydrophilic and lipophilic environments. Again without intending to be bound by theory, it is surmised that thiol may act as a carrier for the Group V metal and may deliver the metal to its target, thereafter becoming available to coordinate with, and provide similar transport and delivery for, another locally available metal. It is also hypothesized that the Group V metal may undergo thiol exchange between the carrier-thiol and thiols involved in biological processes. Indeed, metal thiols might act to inhibit enzymes containing sulfhydryl groups or enzymes that produce sulfur intermediates, both of which are involved in the immune system.

Thus, the system of the invention tends to be in flux over time regarding the local concentration of (a) the complex, (b) uncomplexed thiol, and (c) uncomplexed metal. As explained in more detail below, the overall ratio of metal and thiol used in the immunomodulating agent of the invention may be varied over a wide range depending on the environment in which the agent will be used. The identity of the metal and the thiol may also vary with intended use and local environment. The form that the metal and thiol may take in accordance with the invention, and ways of facilitating complexing of one to the other, are discussed in more detail below.

In situ formation of the complex occurs easily in the presence of moisture. Because of the ability of the complex to form in situ, and because the surprising immunomodulating activity provided by mixing thiol and metal may not be entirely attributable to formation of the complex, the immunomodulating agent of the invention may be supplied in the form of a mere mixture of thiol and metal, or by placing thiol and metal in sufficient proximity that they may interact to provide immunomodulating activity. A "mixture" as used herein includes placing these components close enough to each other that they may interact to modulate the immune system under conditions of use. Naturally, it is preferred that both the metal and the thiol be provided in a form that makes them easily accessible to each other, and facilitates coordinate bonding of one to the other to form the preferred complex.

Alternatively, the immunomodulating agent of the invention may be provided to its site of action in a form that already is primarily comprised of the metal:thiol complex, with only modest amounts of uncomplexed thiol or uncomplexed metal. This form of the invention may be manufactured in a number of ways. For example, metal and thiol may be dissolved in the same solution. Following formation of complex, the complex may be separated from uncomplexed thiol or uncomplexed metal by standard techniques including but not limited to precipitation of one component or the other, use of specific scavengers, adjusting pH, and other techniques to cause precipitation of the complex. In like manner, or by other known techniques, it is possible to remove any anion present in solution due to the metal having been originally supplied in the form of a metal salt. However, it is not strictly necessary to remove such an anion. The existence of such anions in the system, or even the incorporation of such anions into a crystal of a metal:thiol complex (if the complex is provided in powder or crystalline form) should not cause serious diminution of antimicrobial activity. It is expected that both formation and degradation of complex may occur in situ, particularly when the agent of the invention is interacting with the immune system, or is otherwise in use. Thus, the relative concentration of complex, uncomplexed metal and uncomplexed thiol may change over time. It is, of course, possible to supplement one or more of these three ingredients either intermittently or continuously during use.

Either the metal, the thiol or the complex may be supplied in liquid or solid form. The immunomodulating agent of the invention may further include solvents, diluents, excipients, preservatives, emulsifiers, compounds for adjusting odor, taste, pH or the like.

It is not necessary to choose only a single metal or a single thiol for use in the immunomodulating agent of the invention. A plurality of different metals (e.g., bismuth and antimony together) may be used, as may a plurality of thiols (e.g., ethanedithiol and butane dithiol together). Metals and thiols are presented to the system in a variety of different manners. For example, one metal may be presented as a free ion while the other is added in the form of a salt. Even where only a single metal is used, some of it may be added freely and some may be added in salt form. A wide variety of different salts may be used. Likewise, one or more such variations are permitted when presenting the thiol component into the invention.

The Metals
The Presentation of the Metal

Several bismuth, antimony or arsenic salts can be used as the metal component of the invention. Although it is not required that metal be presented in salt form, metal salts are often used to put the metal in solution and make it available and accessible to the complexing agents of the invention which include thiol compounds. The preferred salts of the invention are the ones that make the metal more accessible and available to form a complex with the complexing agent. Examples of salts include, but are not limited to, metal nitrate, subgallate, citrate, oxide and subsalicylate. Preferably, the metal salt is a bismuth salt such as bismuth nitrate, colloidal bismuth subcitrate and bismuth subsalicylate. Bismuth has proven significantly more effective than antimony and arsenic in antimicrobial uses and is expected to be also more effective than antimony and arsenic in the immunomodulating agents of the present invention.

Solubility of the Metal Salt

The activity of the metal:thiol complex is expected to vary with the type of salt being used. One factor that can influence this activity is the solubility of the metal salt under conditions of use or of preparation of complex. One expected advantage for combining metal with complexing agent is the increased solubility of the metal. In addition, one presumes that the more soluble the metal salt is, the more of the metal will be available to complex with the thiol. In this regard, choosing the solvent in which the metal salt is dissolved can also have an effect on the activity based on solubility considerations for the metal salt.

Molar Ratio of the Metal:complexing Agent

Another factor to consider in maximizing the solubility of the metal:complexing agent is its final molar ratio. This ratio is a factor in determining the final concentration of metal salt and thus can have an influence on the solubility of the metal salt. For instance, solubility of the metal salt is a more significant factor (i.e. more difficult to achieve) at high metal concentrations and at higher metal:complexing agent ratios.

The Influence of pH on the Selection of the Metal Salt

Yet another consideration in selecting the metal salt in order to maximize the metal:thiol complex activity is the desired pH of the metal:thiol complex solution being prepared, or the local pH where the invention is to be used, especially where complex is formed in situ. Preferably, the metal salt used has a good buffering capacity at a pH range that encompasses the desired pH of the final complex solution. This way, the salt can also be used as a buffer to maintain the pH of the complex solution within a certain limit. However, the metal salt does not have to act as a buffer in the complex solution particularly when such solution contains another salt that acts as the buffering agent.

It is important to note, however, that while the activity of the metal:thiol complex may vary with the type of salt used, applicant believes that such activity is invariably present. Accordingly, the present invention encompasses the use of any metal salt that is fully or partially, or has the potential to be fully or partially, in solution with the complexing agent in the solvent where the invention will be prepared or used.

The Thiols

The Enhancement of Antibacterial Activity of Bismuth by Thiols and Pyrithione and Preferred Parameters of Enhanced Activity Since the antimicrobial properties of the metal:thiol agent could play a role in its immunomodulating activity, the preferred thiols of the present invention are the ones that give the better antimicrobial activity. It is believed, however, that the invention may treat sepsis and septic shock by other mechanisms in addition to any desirable antimicrobial activity. Applicants have determined that organic thiol compounds can enhance the antibacterial activity of bismuth. Some preferred thiols have one to two sulfhydryl groups, especially two. They are preferably amphipathic and can form coordinate bonds to bismuth, arsenic and antimony. Many are also alcohols, but the presence of a hydroxyl group does not appear to enhance activity. Indeed, some very active compounds, bismuth:propanedithiol and bismuth ethanedithiol contain no hydroxyl groups. However, the hydroxyl group seems to increase the stability of some Bis-thiols, such as bismuth:dimercaprol, without seriously hampering activity. The compounds bismuth: β-mercaptoethanol and bismuth:2-mercaptoethylamine are identical in structure except for the presence of a hydroxyl group with an amino group in bismuth:2-mercaptoethylamine at the same position. This difference amounted to a 5-fold decrease in bismuth:2-mercaptoethylamine activity and a different optimum molar ratio as compared with bismuth:β-mercaptoethanol. Though dimercapto-succinic acid is structurally similar to dimercaprol, the presence of acidic groups largely abolished synergy with bismuth. An oxygen atom (especially when not part of an alcohol group), an amine, and especially an acid group substitution on thiols diminished activity.

Applicants have discovered that dithiols have generally more antimicrobial activity than monothiols, as they are better chelators. Lower levels of dithiols are required than of monothiols to achieve optimum activity. Approximately 3 times as much 3-mercapto-2-butanol as dimercaprol was required to achieve similar inhibitory activity. The compounds DMSA and dimercaptopropane-1-sulfonic acid are dithiols, and excellent bismuth chelators, but did not show antibacterial synergy, nor were they lipophilic. Lipophilicity of bismuth-thiol chelates is a very good predictor of antibacterial activity as discussed in more detail, infra. This model predicts that any hydrophobic monothiol, or any dithiol with at least a modicum of hydrophobicity will be synergistic with bismuth. Applicant also determined that compounds containing three or more thiols, such as trithiocyanuric acid and 2,5-dimercapto-1,3,4-thiadiazole, are also good chelators.

Accordingly, in a preferred embodiment, the present invention provides a composition comprising bismuth chelated by a thiol compound containing one sulfhydryl group such as a compound selected from the group consisting of 3-mercapto-2-butanol, β-mercaptoethanol, 2-mercaptoethylamine, monothioglycerol, and p-chlorothiophenol.

Most preferably, the chelating compound contains a plurality of sulfhydryl groups (for example, two) such as a compound selected from the group consisting of 3,4-dimercaptotoluene, ethanedithiol, 2,3-butanedithiol, 2,3-dimercapto-1-propanol, 1,4-dimercapto-2,3-butanediol, 1,3-propanedithiol, and 1,4-butanedithiol.

As a result of the variation in the levels of enhancement of activity of metal in the presence of different thiols, different models for predicting such enhancement are set forth below:

Vicinity of the Thiol Groups

The compound Bismuth-2,3-BDT (2,3-butanedithiol) appears to be as good as bismuth:ethanedithiol (discussed in more detail hereinafter) against most bacteria. However, Bismuth-1,4-butanedithiol (1,4-butanedithiol) had nearly 100-fold less antibacterial activity, indicating that vicinal dithiols work much better than separated dithiols. Bismuth:propanedithiol (1,3-propanedithiol) works quite well, but not as well as the vicinal dithiols, suggesting that vicinal dithiols work best, followed by those separated by one carbon, while others are less effective.

Accordingly, in a preferred embodiment of the invention, each of two carbon atoms on the chelating thiol compound is linked to one sulfhydryl group, and the carbon atoms linked to the sulfur atoms are separated from each other by 0 to 3 intervening atoms, preferably 0 to 1 intervening atom. Most preferably 0, i.e., where these two carbon atoms are directly covalently linked.

Intensity of Yellow Color

Intensity of yellow color in aqueous solution is predictive of enhanced antimicrobial activity at high molar ratios of bismuth to thiol. Most metal-thiols show an absorbance at 410 nm with an absorption coefficient of 1.0 to 2.6, except for bismuth:dimercaprol and bismuth:propanedithiol, which had larger absorption coefficients (6.2 and 12.4, respectively). Bismuth:dimercaprol and bismuth:propanedithiol work optimally at high bismuth to thiol ratios (3:1 to 2:1). The yellow color is believed to arise from ligand to metal charge-transfer bands (LMCT), which are common to metal ion complexes. For example, the combination of the "soft" $Bi^{3+}$ ion with the "soft" thiolate sulfur should favor ligand to metal charge-transfer bands. Therefore the intensity of yellow color can be used as a measure of the amount of bismuth-thiol complex formed and the extent of chelate formed. In alkaline bismuth-thiol solutions, for example, yellow color can be used to screen for thiols that best chelate bismuth at low concentrations. Accordingly, a 5:10 mM solution of the bismuth:dithiol composition of the present invention has a preferable light absorbance of at least 1.5, more preferably at least 10, at a wavelength of 410 nm.

Solubility in Butanol (Lipopholicity)

One expected advantage for combining metal with thiol is believed to be increased water solubility for the metal. Though lipophilicity of these agents is important for antimicrobial activity, water solubility is an obvious attribute. Solubility under a variety of conditions underscores the versatility and potential usefulness of metal-thiols of the invention. Many formulations and compositions are possible with these agents. Solubility in water is dependent on both pH and composition. For example, bismuth:dimercaprol is soluble in both acid or base, depending on the molar ratio. Also with bismuth:dimercaprol, a powder can be produced that retains most of the antibacterial activity. That bismuth:dimercaprol can be formulated to retain solubility in different environments, adds to the versatility of this class of compounds.

However, it is important to note that the most active antimicrobial bismuth-thiol in each of the bismuth-monothiol or bismuth-dithiol category is also the most soluble in butanol. Therefore solubility in butanol can predict what complexes of Bis-dithiols are maximally synergistic. Accordingly, in a preferred embodiment, a 5:10 mM solution of the bismuth-dithiol results in at least one percent, more preferably at least 10 percent and most preferably at least fifty percent, of a complex partitioning from water into butanol when partitioned using equal volumes of water and butanol at 25° C.

Complexing the Metal with the Thiol

The chelation of bismuth, antimony and arsenic by thiol compounds in the form of a complex enhances their solubility and reduces the necessary dosage of these metals for effective treatment, thus decreasing any toxicity concerns. This chelation can be achieved, for example, by dissolving the thiol compound in a propylene glycol solution of bismuth, antimony or arsenic salt. Thereafter, samples can be further diluted to the desired concentrations using water or propylene glycol.

Molar Ratios of Bismuth-Thiol Combinations

Bismuth-thiol combinations were tested at a wide range of molar ratios to determine optimal antimicrobial activity. Though 4 to 6-fold less toxic when given intraperitoneally to mice than bismuth or dimercaprol alone, bismuth:dimercaprol is most toxic to mice at a 1:2 molar ratio. High thiol content also proved malodorous and irritating to the skin. Addition of bismuth nitrate to the thiol solution eliminated the sulfur odor and the irritating effects of dimercaprol at a 2:1 ratio, but not entirely at a 1:2 ratio. Bismuth-thiol compounds that achieve optimum activity only at higher thiol concentrations may have less utility, due to these unfavorable effects. The data indicate that each component of bismuth:dimercaprol mitigates the unfavorable characteristics of the other.

Accordingly, in a preferred embodiment of the invention, the molar ratio of the metal (preferably bismuth) to the thiol compound (preferably a dithiol) is from approximately 1:3 to approximately 3:1. More preferably, this molar ratio is from approximately 1:3 to approximately 3:1.

Pharmaceutical Use

As will be discussed below, metal:complexing agent can be administered to modulate the immune system in patients in need thereof. In particular, the compositions of the present invention are useful in treating or preventing sepsis and septic shock. The recommended dosages for prophylactic use are the same as the therapeutic doses described herein.

In accordance with one aspect of the invention, once sepsis or septic shock are predicted to occur or in fact do occur, the metal:thiol complexing agent is administered at a dosage sufficient to reach and modulate the immune response. It is however preferable, especially when the need to modulate the immune response is the result of a bacterial infection, to administer the agent of the invention at dosages (0.1–10 mg of metal per Kg of body weight when administered orally. Preferred intravenous dosage ranges from 10 ng to 200 µg, preferably 2 to 200 µg, more preferably 10 to 100 µg of metal per Kg of body weight. Naturally, the attending clinician may raise or lower dosage based on individual patient response.

As used in the invention, a metal:complexing agent of the invention (whether pyrithione or other thiol) may be administered with or without additional carrier or diluent by the oral, systemic, percutaneous, transmucosal, or other typical route. In a pharmaceutical composition for oral administration, a metal:complexing agent is preferably present in a concentration between 5 and 99% by weight relative to total weight of the composition, more preferably between 50 and 99 percent, especially between 80 and 99 percent.

When prepared for percutaneous administration, a metal:complexing agent is preferably present in a concentration between 2 and 20% by weight relative to the total weight of the composition, more preferably between 5 and 15%, especially between 5 and 10%.

The metal:complexing agent can be administered by itself or in the presence of other antibacterial, antiviral or antifungal agents. In one embodiment, additional antifungal agents are added to metal thiol mixtures and/or complexes of the invention.

Intravenous Injection

Sterile solutions can be administered intravenously. The active ingredient may be prepared at a final dose of 10 ng to 200 µg, preferably 2 to 200 µg of metal per Kg of body weight in the form of metal:complexing agent as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

Treatment in accordance with the invention is only desirable until all symptoms of sepsis and septic shock are gone. More extended periods may undesirably further compromise the existence of the natural flora in the body.

Bismuth-Ethanedithiol (BisEDT)

A preferred Bis-thiol composition for modulating the immune system and more specifically treating or preventing sepsis and septic shock is bismuth:ethanedithiol. It is a stronger antimicrobial agent than bismuth:dimercaprol. As discussed earlier, antimicrobial activity, in addition to the immunomodulating activity of Bis-thiols, may play a role in treating or preventing sepsis and septic shock.

In animal experiments, in vivo and in vitro, BisEDT (in molar ratio of 2:1; Bismuth:EDT) in doses of 20 µg/Kg in mice was able to prevent the polymicrobial sepsis induced up-regulation of both pro- and anti-inflammatory cytokines. An imbalance of these cytokines is believed to play a role in the pathogenesis of sepsis and septic shock. In dangerous infections or sepsis inflammatory response syndromes (SIRS), these cytokines may cause immunosuppression resulting in death.

IL-10 is believed to be one of the key players in the cytokine cascade that helps improve the survival from sepsis and septic shock. Splenic macrophages from CLP mice treated with BisEDT do not produce IL-10 in vitro as much as the macrophages from BisEDT untreated CLP animals. However, when the cells from the treated mice were stimulated with lipopolysaccharide, SEB or PMA they did not significantly up-regulate the IL-10 release but the BisEDT untreated group did. Further experiments showed that all CLP mice died when they were treated with both BisEDT and antibodies to IL-10. The mechanism behind this observations is that BisEDT suppressed the surge of IL-10 to a degree and the antibody to IL-10 bound and/or neutralized the small amount of IL-10 present. Therefore, there was no controlling mechanism to prevent the over production of pro-inflammatory cytokines.

Since a large portion of patients become septic and undergo a shock state mostly due to some degree of immuno-incompetence (due to underlying diseases, chemotherapy, and iatrogenic causes) this method of treatment may be beneficial in these patients. Furthermore, since improving the functional activities of immune cells will improve the outcome, BisEDT would be an ideal agent to do so without compromising the host cells.

One of the disadvantages of using ethanedithiol is its foul odor. However, when bismuth and ethanedithiol are combined, it no longer smells. Most every other aspect of bismuth:ethanedithiol is advantageous. Compared to bismuth:dimercaprol, bismuth:ethanedithiol is 50 times cheaper, and no more toxic. bismuth:ethanedithiol lethality to mice is very similar to that of dimercaprol, according to accompanying MSDS sheets from Aldrich Chemical Company. Bismuth:ethanedithiol is less toxic than bismuth-:dimercaprol simply because less is needed. It is also a more stable compound at all molar ratios and pHs.

EXAMPLE 1

Effect of BisEDT Treatment on Survival Rate of Septic Mice

The object was to determine if Bismuth-ethanedithiol (BisEDT) in a molar ratio of 1:2, would protect CLP mice. Mortality rate of greater than 90% is observed within 18–72 hours in this model. A dose response study was performed to determine an optimal dose of BisEDT. After CLP, BisEDT was given via a tail vein, once a day, for three days. The mice were observed for 8 days to determine survival. Data were analyzed using Chi-Square and Krumkal Walkis tests. The data are presented below as average ±SEM. Data compared to control (dose 0) were considered significant (*) at p<0.05.

| Dose (ug/kg BW) | n | Survival (%) | Survival (hrs.) |
| --- | --- | --- | --- |
| 0 | 5 | 0 | 31 ± 93 |
| 2 | 5 | 20 | 64 ± 43 |
| 20 | 5 | 60* | 110 ± 35* |
| 200 | 5 | 40 | 75 ± 21 |
| 2000 | 5 | 20 | 48 ± 24 |

A dose of 20 µg/kg body weight (BW) was found to significantly increase survival. The study was repeated using limited doses to confirm the results of the dose response study, and to determine if more frequent dosing would increase or prolong the survival. These results are shown below.

| Dose (ug/kg BW) | n | Survival (%) | Survival (hrs.) |
|---|---|---|---|
| Injection Once a Day | | | |
| 0 | 5 | 0 | 36 ± 10 |
| 2 | 9 | 56* | 109 ± 29* |
| 200 | 5 | 40 | 75 ± 21 |
| Injection Twice a Day | | | |
| 0 | 5 | 0 | 31 ± 9.4 |
| 2 | 9 | 44* | 103 ± 29* |
| 200 | 5 | 40 | 97 ± 40 |

Analysis of these data produced similar results to that of the dose response study. However, an increase in dose frequency from once daily to twice daily did not increase survival (P=0.73).

Figure 2:
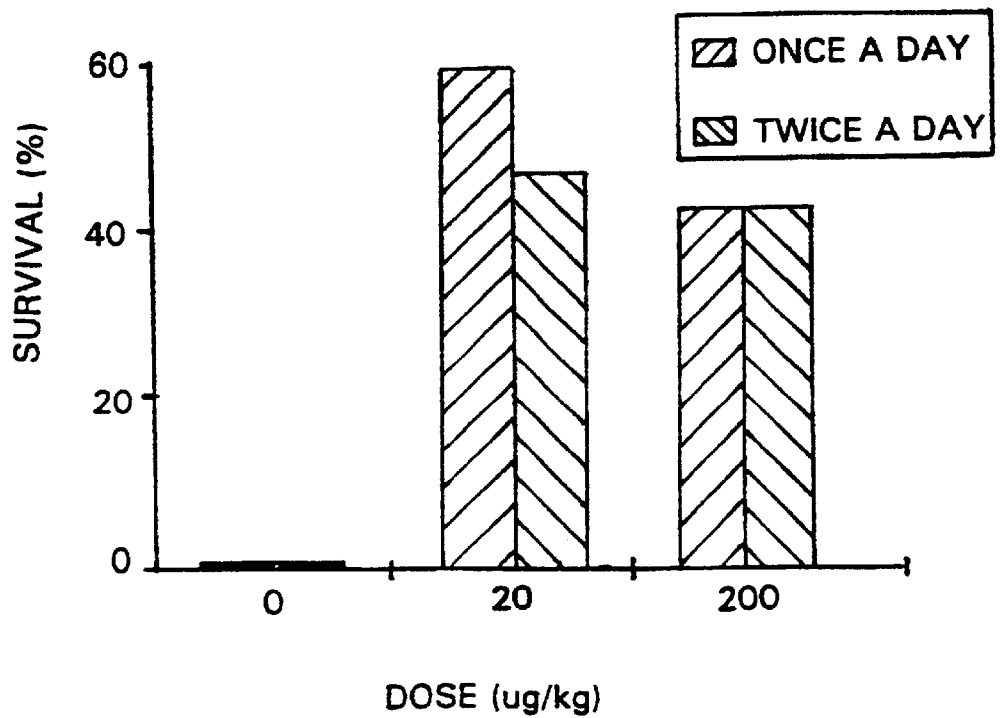
FIG. 2 shows the survival rate of CLP mice treated with different doses of BisEDT for once (left columns) or twice a day (right columns).

FIGS. 1 and 2 summarize some of the results in this Example. Overall, percentage survival increased from 0% (control) to 60% (treatment group) and survivability increased from approximately 36 hours without treatment to 108 hours with treatment. These findings suggest that BisEDT may be an effective treatment for sepsis.

EXAMPLE 2
Effect of BisEDT on Reactive Radical Release in Sepsis

This study was undertaken to determine the effects of BisEDT on reactive radical release in sepsis. Sepsis was induced in twenty 8-week-old mice by cecal ligation and perforation (CLP). Five hours after CLP, BisEDT in a ratio of 1:2 (Bismuth, 20 µg/kg body weight) was administered via tail vein injections in 10 mice while others received vehicle. Another group received only anesthesia (control, n=9). Eighteen hours after injection the mice were sacrificed, spleens collected, cell harvested and macrophages/monocytes purified by density gradient centrifugation. Macrophages/monocytes were plated in 96-well plates with complete RPMI medium. Superoxide (—$O_2$—), hydrogen peroxide ($H_2O_2$ at 60 min) and nitric oxide (as nitrite, $NO_2$— at 16 h) production by the macrophages/monocytes were measured with or without stimulating in vitro with lipopolysaccharide (LPS), staphylococcal enterotoxin B (SEB) or phorbol myristate acetate (PMA). Data were analyzed using ANOVA and Mann-Whitney tests for group and treatment differences and were considered significant at p<0.05. Data showed that macrophages/monocytes from CLP mice produced higher amounts of —$O_2$—, $H_2O_2$ and $NO_2$— compared to control mice.

Figure 3:
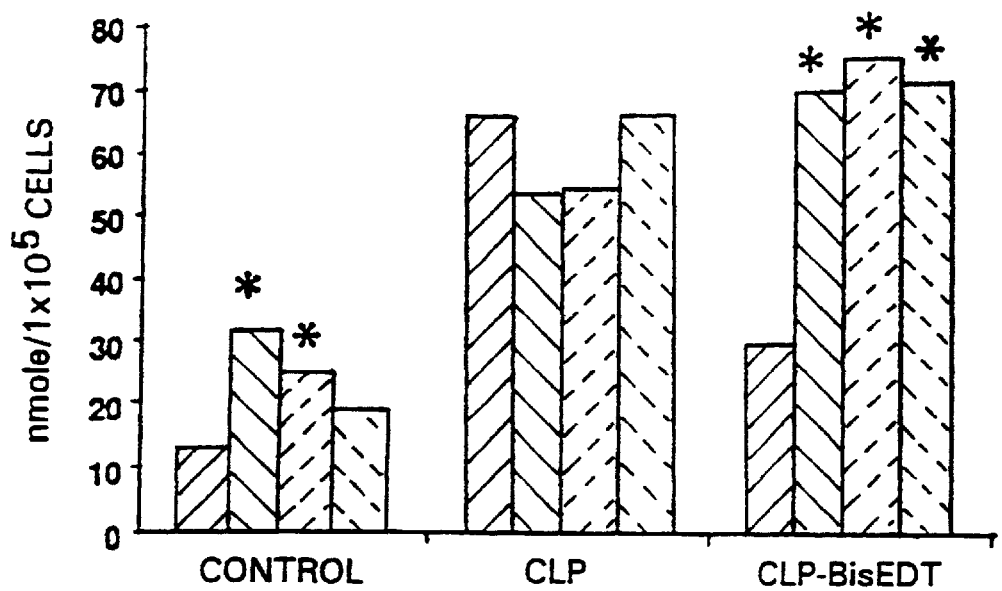
FIG. 3 shows the superoxide production by cultured mouse splenic macrophages from control mice, CLP mice and CLP mice treated with BisEDT.
Figure 4:
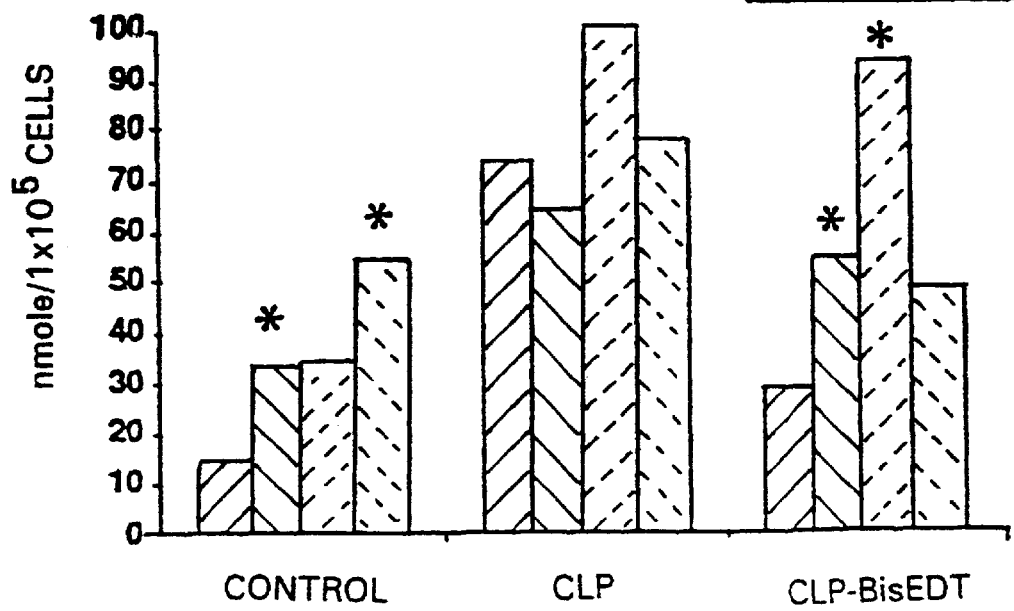
FIG. 4 shows the hydrogen peroxide production by cultured mouse splenic macrophages from control mice, CLP mice and CLP mice treated with BisEDT.
Figure 5:
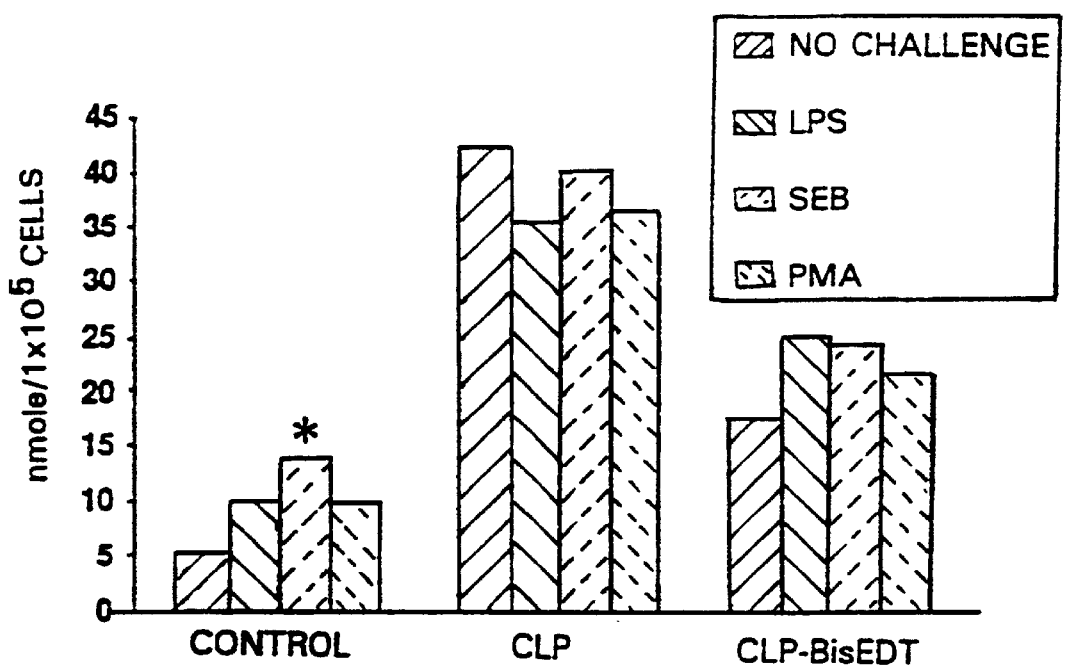
FIG. 5 shows the nitric oxide production by cultured mouse splenic macrophages from control mice, CLP mice and CLP mice treated with BisEDT.
Figure 6:
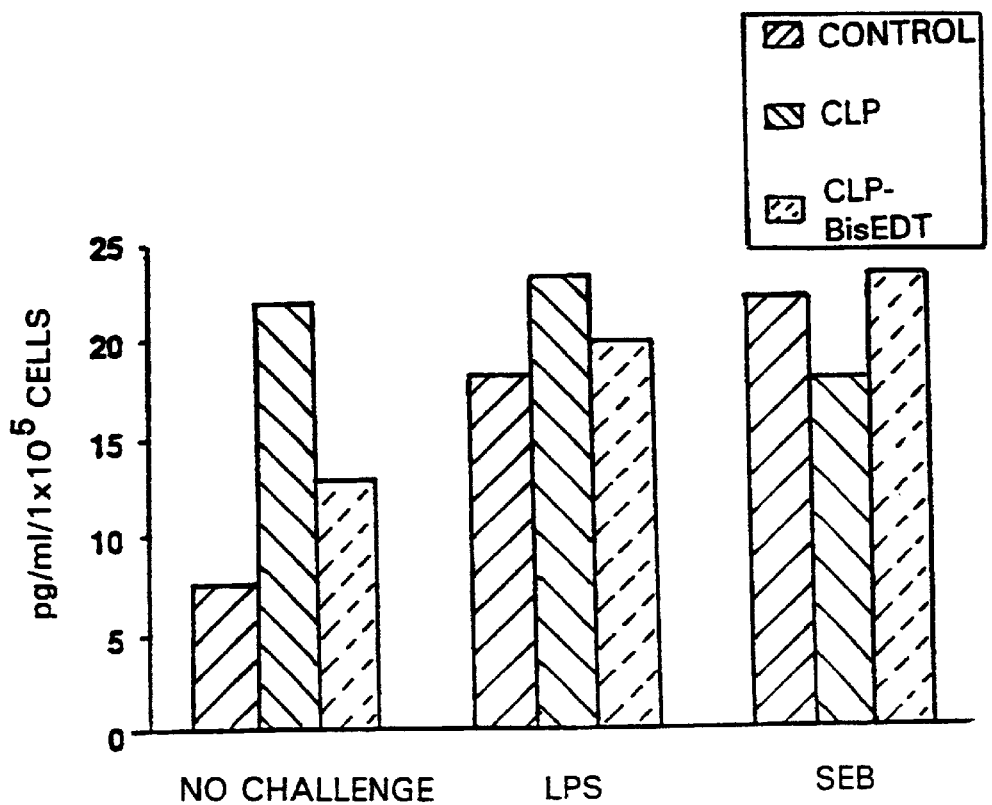
FIG. 6 shows IL-1α release by cultured mouse splenic macrophages from control mice, CLP mice and CLP mice treated with BisEDT.
Figure 7:
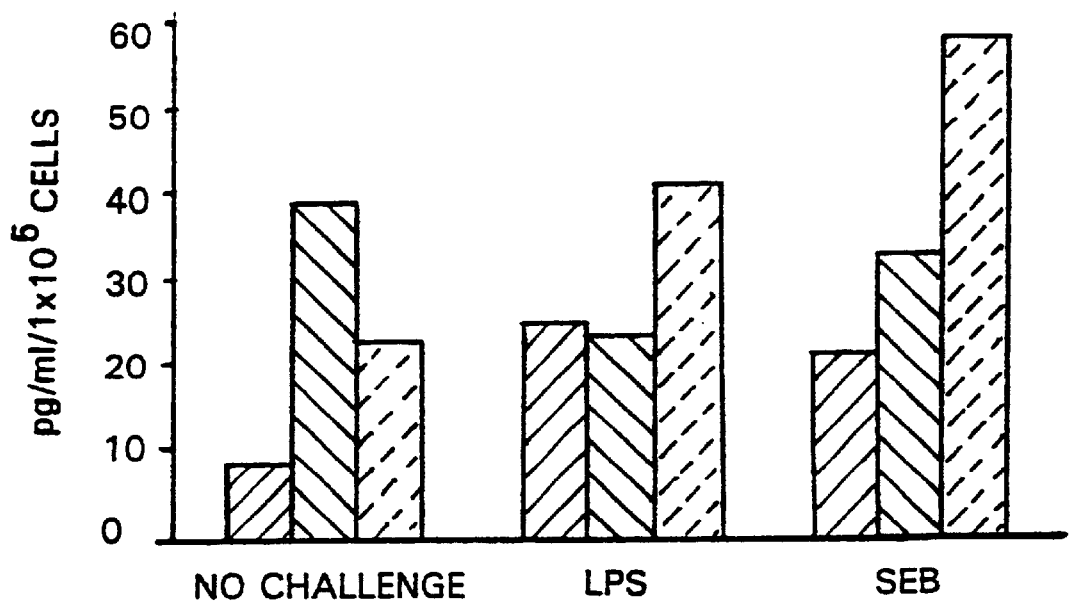
FIG. 7 shows TNFα release by cultured mouse splenic macrophages from control mice, CLP mice and CLP mice treated with BisEDT.
Figure 8:
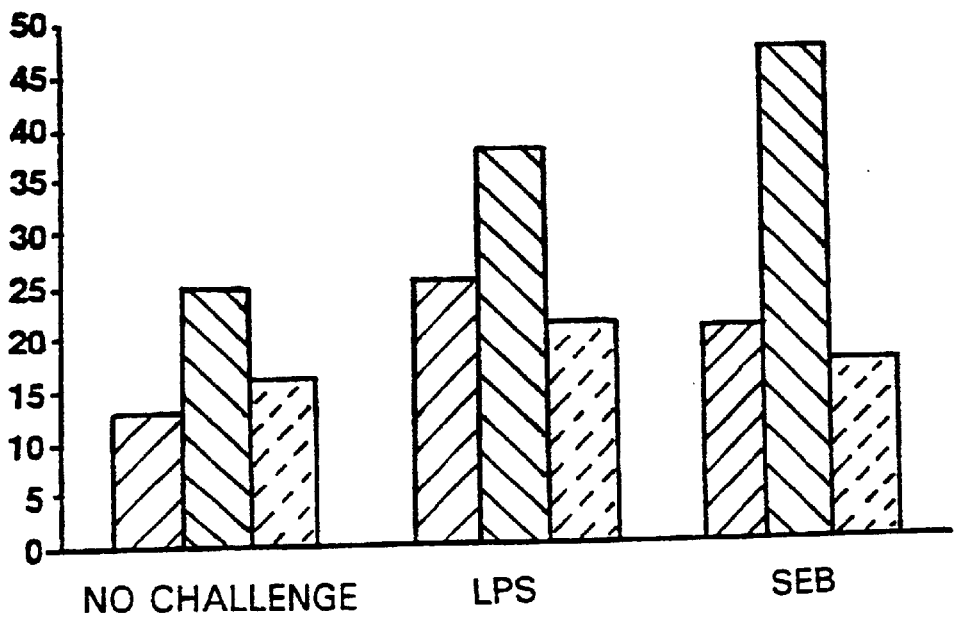
FIG. 8 shows IL-10 release by cultured mouse splenic macrophages from control mice, CLP mice and CLP mice treated with BisEDT.
Figure 9:
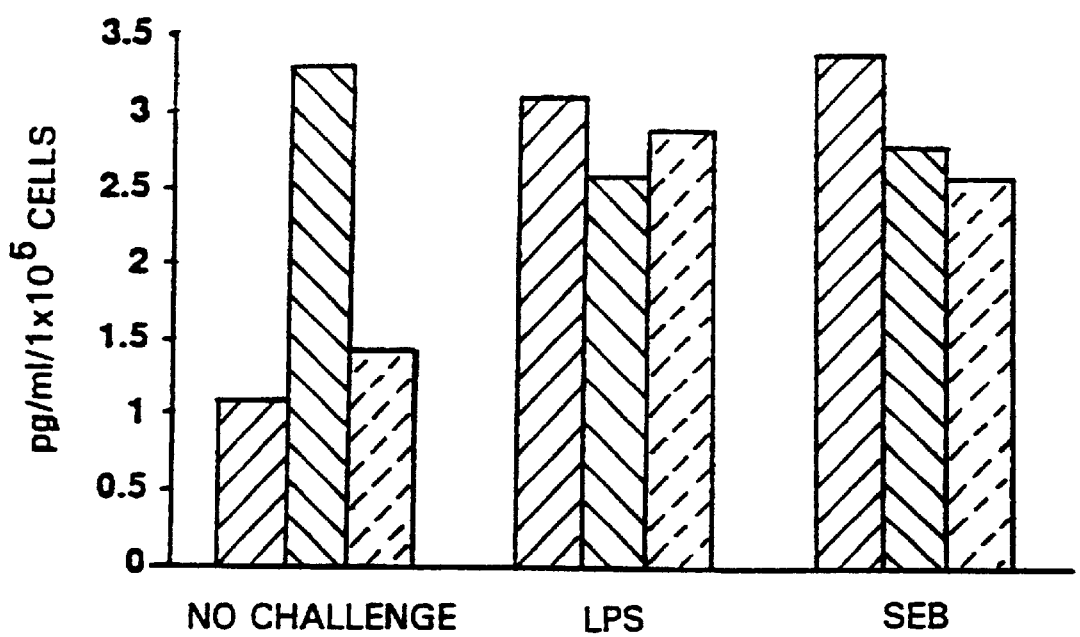
FIG. 9 shows $TGF\beta_1$ release by cultured mouse splenic macrophages from control mice, CLP mice and CLP mice treated with BisEDT.
Figure 10:
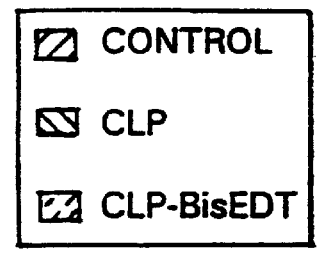
FIG. 10 shows survival in CLP mice treated with BisEDT and anti-IL-10 antibody.
Figure 10:
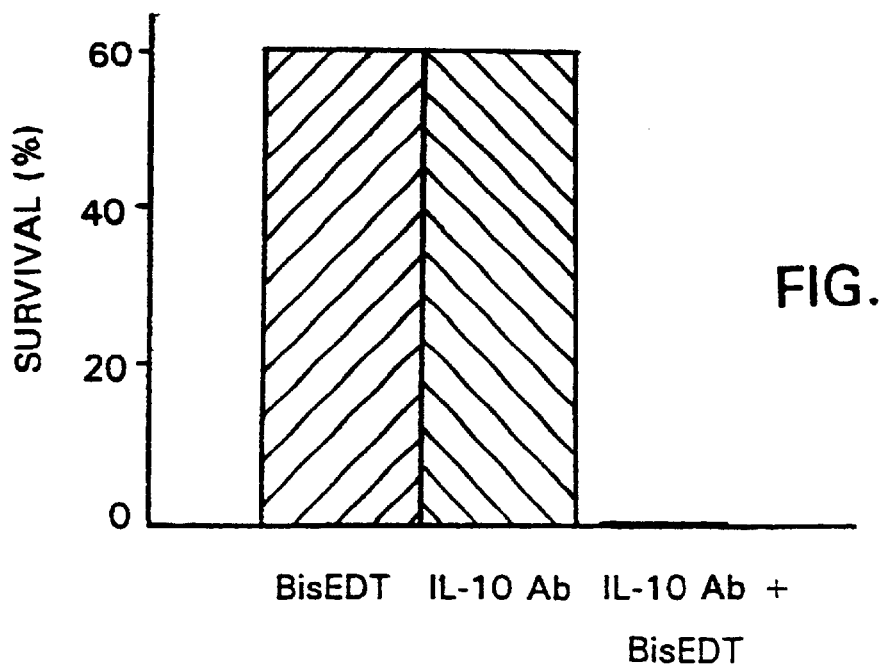

The amounts of these metabolites produced by macrophages/monocytes from BisEDT-treated CLP mice were in between that produced by the control and untreated CLP mice but not significantly different from either of these groups. Nevertheless, when macrophages/monocytes from BisEDT-treated CLP mice were stimulated, release of these metabolites were significantly increased, but macrophages/monocytes from CLP mice did not respond to these stimuli suggesting the development of tolerance in these cells. Stimulated-release of —$O_2$—, $H_2O_2$ or $NO_2$— from the control macrophages/monocytes showed a similar trend to that of the treated mice, however, of much smaller magnitude which may have been related to activating or regulatory factors in vivo. The results or this Example are shown in FIGS. 3–5.

These data suggest that preservation of the cellular responses to activating stimuli in macrophages/monocytes from BisEDT-treated mice may mediate through modulation of factors that protect cells from becoming tolerant or immune suppressed in vivo.

EXAMPLE 3
Role of Cytokines in Sepsis

This study was undertaken to determine the effects of BisEDT on cytokine release in sepsis. Sepsis was induced in mice by cecal ligation and perforation (CLP). Five hours after CLP, BisEDT in a ratio of 1:2 (Bismuth, 20 µg/kg body weight) was administered via tail vein injections in some mice while others received vehicle. Another group received only anesthesia. Eighteen hours after injection the mice were sacrificed, spleens collected, cell harvested and macrophages/monocytes purified by density gradient centrifugation. Macrophages/monocytes were plated in 96-well plates with complete RPMI medium. Various cytokine serum levels and production by the macrophages/monocytes were measured with or without stimulating in vitro with lipopolysaccharide (LPS), staphylococcal enterotoxin B (SEB), or phorbol myristate acetate (PMA). Data were analyzed using ANOV and Mann-Whitney tests for group and treatment differences (*) were considered significant at p<0.05.

Serum Cytokine Levels (pg/ml) in Mice Treated with BisEDT

| | IL-1α | TNFα | IL-10 | TGFβ$_1$ |
|---|---|---|---|---|
| Control | 6.8 ± 1.6 | 3.6 ± 2.1 | 22.9 ± 2.7 | 40.6 ± 9.5 |
| CLP | 12.2 ± 1.3* | 19.4 ± 3.4* | 311 ± 165* | 17.2 ± 3.0* |
| CLP + BisEDT | 10.5 ± 1.1 | 13.7 ± 2.9* | 165 ± 69 | 24.8 ± 3.6 |

These experiments identified IL-10 as being one of the key players in the cytokine cascade that helps improve the survival from sepsis and septic shock. They demonstrate that splenic macrophages from CLP mice treated with BisEDT do not produce IL-10 in vitro as much as the macrophages from BisEDT untreated CLP animals. However, when the cells from the BisEDT treated CLP mice were stimulated with lipopolysaccharide, SEB or PMA they did not significantly up-regulate the IL-10 release but the BisEDT untreated CLP mice group did. Further experiments showed that all CLP mice died when treated with both BisEDT and antibodies to IL-10. The results of all these experiments are summarized in FIGS. 6–10. A possible mechanism behind this observations is that BisEDT suppressed the surge of IL-10 to a degree and the antibody to IL-10 bound and/or neutralized the small amount of IL-10 present. Therefore, there was no controlling mechanism to prevent the over production of pro-inflammatory cytokines.

The invention has ben described in terms of preferred embodiments thereof, but is more broadly applicable as will be understood by those of skill in the art. The scope of the invention is therefore limited only by the pertinent claims.

What is claimed is:

1. A method of treating or preventing sepsis or septic shock comprising administering to a patient in need of said treatment or prevention, an effective amount of a formulation comprising an immunomodulating agent selected from the group consisting of:
   (A) a mixture comprising (i) a complexing agent having at least one thiol group, and (ii) a group V metal or compound thereof said Group V metal being selected from the group consisting of bismuth, antimony and arsenic;
   (B) a complex whose molecular structure includes (i) a complexing agent having at least one thiol group, (ii) a Group V metal or compound thereof said Group V metal being selected from the group consisting of bismuth, arsenic and antimony; and (iii) a coordinate bond linking at least one sulfur atom of the thiol-containing complexing agent of subparagraph (B) (i) to the metal of subparagraph (B) (ii); and (C) a combination comprising the complex of paragraph (B) and at least one specie selected from the group consisting of (i) a thiol-containing complexing agent and (ii) a Group V metal or compound thereof, said Group V metal, being selected from the group consisting of bismuth, antimony and arsenic.

2. The method of claim 1, wherein the molar ratio of Group V metal to thiol-containing complexing agent in said formulation is between 1:3 and 3:1.

3. The method of claim 1, wherein the molar ratio of Group V metal to thiol-containing complexing agent in said formulation is between 1:1 and 3:1.

4. The method of claim 1, wherein the molar ratio of Group V metal to thiol-containing complexing agent in said formulation is between 2:1 and 3:1.

5. The method of claim 1, wherein the thiol-containing completing agent of each of paragraphs (A), (B) and (C) has, in its molecular structure, at least two sulfhydryl groups.

6. The method of claim 1, wherein the Group V metal of each of paragraphs (A), (B) and (C) is bismuth.

7. The method of claim 1, wherein the Group V metal of each of paragraphs (A), (B) and (C) is antimony.

8. The method of claim 1, wherein the Group V metal of each of paragraphs (A), (B) and (C) is arsenic.

9. The method of claim 1, wherein the Group V metal of each of paragraphs (A), (B) and (C) is bismuth and wherein the thiol-containing complexing agent of each of paragraphs (A), (B) and (C) has at least two sulfhydryl groups in its molecular structure.

10. The method of claim 5, wherein one sulfhydryl group is bound to a first carbon atom and another sulfhydryl group is bound to a second carbon atom, and wherein said first carbon atom is separated from said second carbon atom by 0–3 intervening atoms.

11. The method of claim 10, wherein said first carbon atom is separated from said second carbon atom by 0–1 intervening atoms.

12. The method of claim 1, wherein the thiol-containing complexing agent of each of paragraphs (A), (B) and (C) is selected from the group consisting of 3,4-dimercaptotoluene, trithiocyanuric acid, 2,5-dimercapto-1,3,4-thiadiazole, 2,3-dimercapto-1-propanol, 3-mercapto-2-butanol, β-mercaptoethanol, 2-mercaptoethylamine, and 1-monothioglycerol, ethanedithiol, 2,3-butanedithiol, 1,4-butanedithiol, 1,4-dimercapto-2,3-butanediol, 1,2-propanedithiol, 1,3-propanedithiol, and p-chlorothiophenol.

13. The method of claim 1, wherein the thiol-containing complexing agent of each of paragraphs (A), (B) and (C) is ethanedithiol and the Group V metal of each of paragraphs (A), (B) and (C) is bismuth.

14. The method of claim 13, wherein the molar ratio of bismuth to ethanedithiol in said formulation is from 1:3 to 2:1.

15. The method of claim 14, wherein the molar ratio of bismuth to ethanedithiol in said formulation is 2:1.

16. The method of claim 13, wherein said bismuth:ethanedithiol is administered intravenously.

17. The method of claim 16, wherein said bismuth:ethanedithiol is administered at a dose of 10 ng–200 $\mu$g/Kg of body weight.

18. A method of modulating the immune response in a subject comprising administering to said subject a formulation comprising an immunomodulating agent selected from the group consisting of:

(A) a mixture comprising (i) a complexing agent having at least one thiol group, and (ii) a group V metal or compound thereof said Group V metal being selected from the group consisting of bismuth, antimony and arsenic;

(B) a complex whose molecular structure includes (i) a complexing agent having at least one thiol group, (ii) a Group V metal or compound thereof said Group V metal being selected from the group consisting of bismuth, arsenic and antimony; and (iii) a coordinate bond linking at least one sulfur atom of the thiol-containing complexing agent of subparagraph (B)(i) to the metal of subparagraph (B)(ii); and (C) a combination comprising the complex of paragraph (B) and at least one specie selected from the group consisting of (i) a thiol-containing complexing agent and (ii) a Group V metal or compound thereof, said Group V metal, being selected from the group consisting of bismuth, antimony and arsenic.

19. The method of claim 18, wherein modulation of the immune system comprises preventing the surge of pro-inflammatory cytokines, anti-inflammatory cytokines, oxygen radicals, and nitrate radicals.

* * * * *